(12) United States Patent  (10) Patent No.: US 9,211,175 B2
Stopek et al.  (45) Date of Patent: Dec. 15, 2015

(54) SELF-DETACHABLE MEDICAL DEVICES

(75) Inventors: Joshua Stopek, Guilford, CT (US);
Daniel Broom, Branford, CT (US);
Amin Elachchabi, Hamden, CT (US);
Thomas Casasanta, Kensington, CT
(US); Garrett Ebersole, New Haven, CT
(US)

(73) Assignee: Covidien LP, Mansfield, MA (US)

( * ) Notice: Subject to any disclaimer, the term of this patent is extended or adjusted under 35 U.S.C. 154(b) by 952 days.

(21) Appl. No.: 13/173,659

(22) Filed: Jun. 30, 2011

(65) Prior Publication Data

US 2012/0010637 A1  Jan. 12, 2012

Related U.S. Application Data

(60) Provisional application No. 61/362,485, filed on Jul. 8, 2010.

(51) Int. Cl.
*A61B 17/08* (2006.01)
*A61F 2/00* (2006.01)

(52) U.S. Cl.
CPC .............. *A61F 2/0063* (2013.01); *A61F 2/0045* (2013.01); *A61F 2210/0004* (2013.01); *A61F 2250/0067* (2013.01); *A61F 2250/0071* (2013.01)

(58) Field of Classification Search
CPC ........... A61F 2250/0071; A61F 2/0063; A61F 2250/0067
USPC ...................... 606/151, 228; 623/23.74, 23.72
See application file for complete search history.

(56) References Cited

U.S. PATENT DOCUMENTS

| 3,887,699 | A | 6/1975 | Yolles |
| 4,767,628 | A | 8/1988 | Hutchinson |
| 5,743,917 | A * | 4/1998 | Saxon ........................... 128/898 |
| 6,264,702 | B1 | 7/2001 | Ory et al. |
| 6,270,792 | B1 | 8/2001 | Guillemet et al. |
| 6,500,777 | B1 | 12/2002 | Wiseman et al. |
| 7,041,868 | B2 | 5/2006 | Greene et al. |
| 7,252,837 | B2 | 8/2007 | Guo et al. |
| 7,279,177 | B2 | 10/2007 | Looney et al. |
| 7,556,598 | B2 | 7/2009 | Rao |
| 2002/0131988 | A1 | 9/2002 | Foster et al. |
| 2003/0100955 | A1 * | 5/2003 | Greenawalt et al. ........ 623/23.74 |
| 2003/0157178 | A1 * | 8/2003 | Chen et al. ..................... 424/486 |
| 2004/0010306 | A1 * | 1/2004 | Freyman et al. .............. 623/1.15 |
| 2004/0054376 | A1 * | 3/2004 | Ory et al. ....................... 606/151 |
| 2004/0098118 | A1 | 5/2004 | Granada et al. |
| 2004/0224007 | A1 | 11/2004 | Zhang |

(Continued)

FOREIGN PATENT DOCUMENTS

FR   2 857 851 A1   1/2005
WO   93/11805      6/1993

(Continued)

OTHER PUBLICATIONS

European Search Report for EP 11250641.5-2320 date of completion is Nov. 29, 2011 (3 pages).

(Continued)

*Primary Examiner* — Gregory Anderson
*Assistant Examiner* — Christina Lauer

(57) ABSTRACT

The present disclosure relates to self-detachable medical devices containing a detachable film layer and polymeric film layer.

24 Claims, 7 Drawing Sheets

(56) References Cited

U.S. PATENT DOCUMENTS

| | | |
|---|---|---|
| 2005/0244455 A1 | 11/2005 | Greenawalt |
| 2005/0261782 A1 | 11/2005 | Hoganson |
| 2006/0034887 A1 | 2/2006 | Pelissier |
| 2006/0116696 A1 | 6/2006 | Odermatt et al. |
| 2006/0121078 A1 | 6/2006 | Trogolo et al. |
| 2006/0188546 A1 | 8/2006 | Giroux |
| 2006/0224038 A1 | 10/2006 | Rao |
| 2007/0129736 A1 | 6/2007 | Solecki |
| 2007/0198040 A1 | 8/2007 | Buevich et al. |
| 2007/0244548 A1 | 10/2007 | Myers et al. |
| 2007/0299542 A1* | 12/2007 | Mathisen et al. .......... 623/23.75 |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0199506 A1 | 8/2008 | Horres et al. |
| 2009/0036996 A1 | 2/2009 | Roeber |
| 2009/0142385 A1 | 6/2009 | Gross et al. |
| 2009/0163936 A1 | 6/2009 | Yang et al. |
| 2010/0003308 A1 | 1/2010 | Tapolsky et al. |
| 2010/0089409 A1 | 4/2010 | Bertagnoli |

FOREIGN PATENT DOCUMENTS

| | | |
|---|---|---|
| WO | WO 02/34304 | 5/2002 |
| WO | WO 2006/020922 A2 | 2/2006 |
| WO | WO 2006/036967 | 4/2006 |
| WO | WO 2010/093333 A1 | 8/2010 |

OTHER PUBLICATIONS

Cohen et al., Dis Colon Rectum Jun. 2005; 48(6): 1130-9. Title: Prevention of Postoperative Abdominal Adhesions by a Novel, Glycerol/Sodium Hyaluronate/Carbonxymethylcellulose-Based Bioresorbable Membrane: A Prospective, Randomized, Evaluator-Blinded Multicenter Study.

* cited by examiner

BODILY FLUIDS

SELF-DETACHABLE MEDICAL DEVICES

CROSS-REFERENCE TO RELATED APPLICATIONS

This application claims the benefit of and priority to U.S. Provisional Patent Application No. 61/362,485, filed Jul. 8, 2010, the entire disclosure of which is incorporated by reference herein.

BACKGROUND

1. Technical Field

The present disclosure relates to medical devices, and more particularly, to self-detachable medical devices including an implantable substrate, a detachable layer, a polymeric film layer, and at least one therapeutic agent.

2. Background of Related Art

A variety of medical conditions may be treated, at least in part, by implanting a medical device into the body of an afflicted patient. Medical devices may be implanted into the body temporarily or left in the body for extended periods of time, even indefinitely. For example, a surgical mesh may be made from non-biodegradable materials and may be implanted into the abdomen of a patient to repair any type of hernia. The mesh may be either placed over the defect (anterior repair) or under the defect (posterior repair).

Such devices may be coated with a therapeutic agent. However, therapeutic coatings may be limited in concentration of the therapeutic agent, may weaken the integrity of the device and may also be unable to provide prolonged release of the agent. It would be beneficial to provide a self-detachable medical device which includes high payloads of a therapeutic agent and which may be capable of providing sustained release of the agent following implantation without compromising the integrity of the implant.

SUMMARY

Accordingly, the present disclosure describes self-detachable medical devices which include an implantable substrate having a surface and a first detachable layer positioned on at least a portion of the surface. The device further includes a second polymeric layer positioned on at least a portion of the first detachable layer, so that upon dissolution of the first layer, the polymeric layer and the substrate may be separated from one another to form two devices. At least one of the substrate, the first detachable layer and the second polymeric layer includes at least one therapeutic agent. In embodiments, the polymeric layer may also be attached to a portion of the medical device surface.

In embodiments, the self-detachable medical devices described herein may include a surgical mesh having a surface and a first detachable layer positioned on at least a portion of the surface. A second polymeric layer may be positioned on at least a portion of the first detachable layer, wherein at least one of the first detachable layer and the second polymeric layer includes at least one therapeutic agent. The polymeric layer may be continuous or discontinuous.

Also disclosed are methods of delivery of a therapeutic agent which include implanting a self-detachable medical device into tissue. The self-detachable medical device includes a first detachable layer positioned on at least a portion of the medical device, a second polymeric layer positioned on at least a portion of the first detachable layer, and at least one therapeutic agent included in at least one of the first detachable layer and the second polymeric layer.

BRIEF DESCRIPTIONS OF THE DRAWINGS

These and other characteristics of the present invention will be more fully understood by reference to the following detailed description in conjunction with the attached drawings, in which.

DETAILED DESCRIPTION

Figure 1:
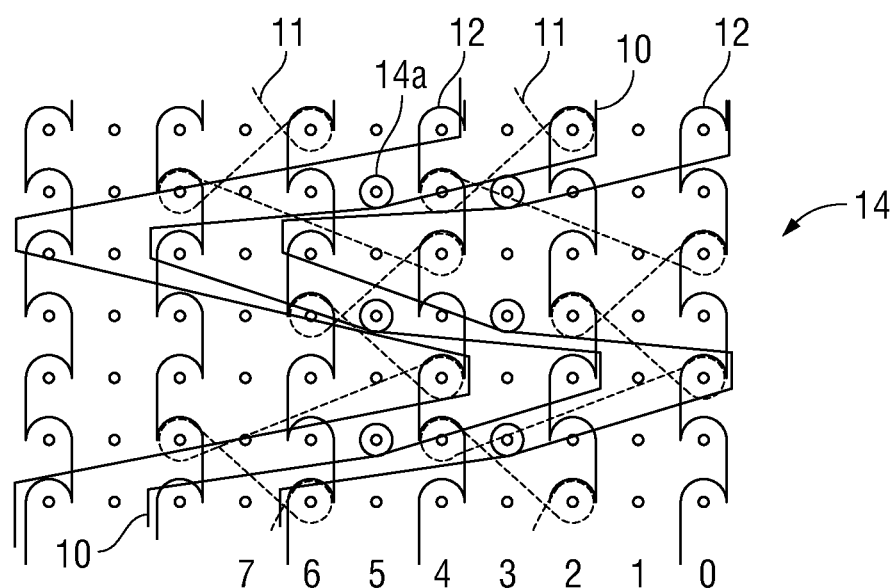
FIG. 1 is a diagram showing the weave of three sheets forming a medical device according to one embodiment described in the present disclosure.

The present disclosure relates to medical devices that include an implantable substrate. A first detachable layer is positioned on at least a portion of the substrate and a second polymeric layer is positioned on at least a portion of the first detachable layer. At least one therapeutic agent may be combined with any of the substrate, the first detachable layer and the second polymeric layer.

The medical devices described herein are self-detachable. By self-detachable, the substrate, the detachable layer and the polymeric film layer may become separated following implantation. At the site of implantation, the medical device may be exposed to bodily fluids, such as blood, water, mucous, urine, sweat, bile, and the like. Exposure to bodily fluids may change the detachable layer from a solid to a liquid. In certain embodiments, since the detachable layer is positioned between the substrate of the medical device and the polymeric layer, dissolution of the detachable layer detaches the polymeric layer from the substrate.

By implantable, the medical devices described herein may be positioned, for any duration of time, at a location within a body, such as within a portion of the abdominal cavity. Furthermore, the terms "implantation" and "implanted" refer to the positioning, for any duration of time, of a medical device at a location within a body, such as within a portion of the abdominal cavity.

The medical devices described herein include an implantable substrate having an outer surface coated with multiple layers. Any medical device suitable for insertion into a patient's body, whether on a temporary or a permanent basis, may be coated with the multiple layers described herein. Some non-limiting examples include soft tissue repair devices such as sutures, staples, meshes, patches, pledgets, buttresses, clips, clamps, screws, and pins. Other suitable devices include staple line reinforcements, tissue fillers, tissue wraps for solid organs or luminal structures, sealing devices, cavity wall and floor reinforcements, intramuscular conduits, access devices, wound closure devices, and the like. The medical devices described herein may be porous, non-porous or composites.

In certain embodiments, the medical device is a surgical mesh. The surgical mesh described herein may include porous fabrics made from intertwined filaments. The filaments may extend horizontally and vertically in a manner which produces sections where the filaments cross-over one another creating points of common intersection. The surgical mesh may be woven, non-woven, knitted or braided. In some embodiments, the filaments may form two-dimensional or three-dimensional meshes. Some examples of two-dimensional and/or three-dimensional mesh substrates may be found in U.S. Pat. Nos. 7,021,086, 6,596,002, 7,331,199, the entire contents of which are incorporated by reference herein.

Suitable meshes for use in the present disclosure include, for example, a collagen composite mesh such as PARIETEX™ Composite Mesh (commercially available from Tyco Healthcare Group LG, d/b/a Covidien). PARIETEX™ Composite Mesh is a 3-dimensional polyester weave with a resorbable collagen film bonded on one side. Another suitable mesh includes Parietex Progrip™ self-fixating mesh (also commercially available from Covidien). Parietex Progrip™ is a polyester mesh which includes poly lactic acid (PLA) microgrips. Other suitable meshes include those sold under the names PARIETENE®, PARIETEX™, SURGIPRO™ (all commercially available from Covidien); PROLENE™ (commercially available from Ethicon, Inc.); MARLEX®, DULEX®, 3D MAX® mesh, PERFIX® plug, VENTRALEX®, and KUGEL® patch (all commercially available from C.R. Bard, Inc.); PROLITE™, PROLITE ULTRA™ (all commercially available from Atrium Medical); COMPOSIX®, SEPRAMESH®, and VISILEX® (all commercially available from Davol, Inc.); and DUALMESH®, MYCROMESH®, and INFINIT® mesh (all commercially available from W.L. Gore). Additionally, meshes within the scope and context of this disclosure may include biologic materials such as allografts (i.e., AlloDerm® Regenerative Tissue Matrix from Lifecell), autografts, and xenografts (i.e., PERMACOL™, from Covidien). In alternate embodiments, processed/purified tissues may also be employed.

In certain preferred embodiments, Parietex™ Composite Mesh or Parietex™ Pro-grip may be utilized in accordance with the present invention.

The filaments may be monofilaments or multi-filaments and, in embodiments, a plurality of multi-filaments may be combined to form yarns. It is envisioned that the mesh may be configured to any size and/or shape suitable for hernia repair. The filaments may comprise core/sheath constructs.

In certain embodiments, the medical device may be a surgical mesh knitted on a warp knitting machine, of the tricot or Raschel type, with at least three sheets or warps of yarn and as many guide bars.

A rear bar is threaded, one guide full and one guide empty, with first mono- or multi-filaments 10 of a biocompatible polymer as represented as a solid line in FIG. 1. An intermediate bar is threaded, one guide full, three guides empty, with second mono- or multi-filiments 11 of a biocompatible polymer as represented as a broken line in FIG. 1. The intermediate bar works in such a way as to obtain a zigzag openwork pattern between the columns of meshes. Finally, a front bar is threaded, one guide full, one guide empty, and works in a chain stitch with third mono- or multi-filaments 12 a biocompatible polymer as represented by a thin line in FIG. 1. The third filament 12, i.e., a chain stitch, imprisons first filament 10 and maintains the length of the mesh while contributing to the formation of the mesh with the intermediate sheet formed by the second filament 11. The different filaments may form yarns and may be worked according to the following chart:

| Warp | | |
|---|---|---|
| Rear bar I | Intermediate bar II Raschel | Front bar III |
| Front bar I | Intermediate bar II | Rear bar III |
| 7 | 3 | 1 |
| 7 | 2 | 0 |
| — | — | — |
| 3 | 4 | 0 |
| 4 | 5 | 1 |
| — | — | — |
| 0 | 1 | |
| 0 | 0 | |
| — | — | |
| 4 | 2 | |
| 3 | 3 | |
| | — | |
| | 1 | |
| | 0 | |
| | — | |
| | 4 | |
| | 5 | |

The rear bar places the first filament or yarn in partial weft under the chain stitch and "thrown" onto the needle not forming a chain stitch. For this reason, at the next row, the needle not forming a chain stitch not being supplied permits escape of the filament which forms a loop 14a projecting from the front face of the mesh.

The threading—one guide full, three guides empty—in the intermediate bar, associated with the displacement, makes it possible to form a light ground texture, stable in width, and open-worked to permit good tissue integration.

The mesh 14 thus obtained may be provided with loops 14a (FIG. 2) which may be perpendicular to one of the mesh surfaces. Loops 14a may hold at a right angle which may be obtained by the rigidity or nerve of the filaments employed. This rigidity may be necessary for the subsequent formation of spiked naps which ensure a grip function.

Figure 2:
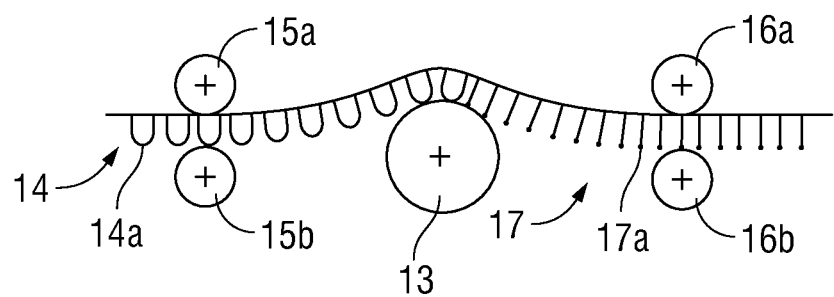
FIG. 2 is a diagrammatic side view of a device permitting the formation of spiked naps on the medical device of FIG. 1 according to another embodiment described in the present disclosure.

On leaving the loom, mesh 14 may be subjected to a thermosetting operation which stabilizes the mesh length and width. The mesh may then be subjected to a phase of formation of the spiked naps consisting, as is shown in FIG. 2, in passing the mesh over a cylinder 13 containing an electrical heating resistor. Mesh 14 is pressed flat on cylinder 13 by two pairs of rollers, upstream 15a, 15b and downstream 16a, 16b, respectively, which are vertically displaceable for controlling this pressing force.

This control as well as that of the temperature of the resistor placed in cylinder 13 and of the speed of movement of mesh 14 across cylinder 13 make it possible to melt the head of each of loops 14a so that each loop 14a forms two spiked naps 17.

Each spiked nap 17 thus may have a substantially rectilinear body protruding perpendicularly with respect to mesh 14 and, at the free end of this body, a head 17a of greater width than that of the body. Head 17a has a generally spheroidal shape or a mushroom shape. Spiked naps 17 gives mesh 14 the ability to attach to tissue when implanted. In addition, spiked naps 17 may attach to other portions of mesh 14 when folded or rolled. In embodiments, the detachable layer may be positioned on the portion of the mesh which includes spiked naps. In other embodiments, the detachable layer may be positioned on the portion of the mesh which does not include the spiked naps.

The first detachable layer may be positioned on any portion of the surface of the medical device. In some embodiments, the detachable layer may form a continuous layer. For example, the detachable layer may form a continuous layer on the surface of a surgical mesh, wherein the porosity of the mesh is occluded by the continuous film. In other embodiments, the detachable layer may form a discontinuous layer covering intermittent portions of the surface of the medical device. In one example, the detachable layer may form a discontinuous layer on the surface of a surgical mesh, wherein the porosity of the mesh is maintained by the discontinuous film.

By detachable, or dissolvable, the first layers described herein may be reduced from a solid or gel to a liquid or gas following interaction with bodily fluids located at the site of implantation. In embodiments, the second polymeric layer may be positioned only on the first detachable layer. In such embodiments, dissolution of the first layer may allow for the complete release or detachment of the second polymeric layer from the surface of the medical device.

In alternate embodiments, the first layer may comprise a hydrogel. Upon implantation and uptake of bodily fluids and/or water or saline, the hydrogel may swell and detach from the surface of the medical device and/or the polymeric layer. Upon detachment, the first and the second layers are released from contact with the surface of the medical device. Hydrogels may comprise bioabsorbable polymers such as those listed herein.

In some embodiments, portions of the second polymeric layer may be positioned on the first detachable layer and portions of the second polymeric layer may be positioned on the surface of the medical device. In such embodiments, dissolution of the first layer may allow for the release or detachment of only portions of the second polymeric layer and/or may create open pores between the surface of the medical device and the second polymeric layer to promote tissue ingrowth.

The first detachable layer may contain any material suitable to dissolve when positioned at the site of implantation and/or exposed to body fluids. Some non-limiting examples of suitable materials used to form the detachable layer include polysaccharides, proteins, peptides, and combinations thereof. In embodiments, the detachable layer may include polysaccharide films capable of dissolving upon implantation. Some non-limiting examples of suitable film materials include cellulose, dextran, chitin, chitosan, alginate, pectin, mucilage, pullanan, methylcellulose, carboxymethylcullose, hydroxypropyl methylcellulose, hydroxyethyl methylcellulose, arabinoxylans, bacterial polysaccharides and combinations thereof. In certain embodiments, the detachable layer may include carboxymethylcellulose.

In other embodiments, the detachable layer may include proteins, such as collagen, elastin, fibrin, albumin, fibrinogen, thrombin, silk, and combinations thereof. In particularly useful embodiments, the detachable layer may include a dissolvable collagen.

The term "collagen" is meant to include any type of collagen, whether natural or synthetic, of human or animal origin, such as, for example, enriched human collagen of type I, human collagen of type III, also enriched, human collagen of type I+III or of type IV or other collagens such as animal collagen of type I or of type I+III. The collagen may be oxidized or non-oxidized.

In certain embodiments, the collagen may be oxidized without crosslinking. For example, native collagen may be dipped in an acid solution and/or washed, to eliminate the telopeptides, notably by pepsin digestion.

The collagen may also be modified by oxidative cleavage. For this purpose periodic acid or one of its salts can be used, applying the technique described by M. TARDY et al. (FR-A-2 601 371 and U.S. Pat. No. 4,931,546, the entire contents of which are hereby incorporated by reference).

It is recalled briefly that this technique consists of mixing the collagen in acid solution with a solution of periodic acid or one of its salts at a concentration of between 1 and $10^{-5}$M, preferably between 5 $10^{-3}$ and $10^{-1}$ M, at a temperature of between 10 and 25° C. for 10 minutes to 72 hours.

This process breaks down some of the collagen's components, these being hydroxylysine and the sugars, thus creating reactive sites without causing crosslinking.

The oxidative cleavage of collagen allows moderate crosslinking later in the collagenic material but does not exclude the possibility of providing this function by other means of moderate cross-linking, for example by beta or gamma irradiation, or other agents of moderate cross-linking, for example chemical reagents at suitably low and non-toxic doses.

For some applications, the detachable layer of the medical devices described herein may be made of collagen which is not oxidized or a mixture in any proportions of non-oxidized and oxidized collagens.

In still other embodiments, the detachable layer may also comprise a water-soluble polymer.

The medical devices described herein also include a polymeric film layer which may be made from any biodegradable polymer. The biodegradable polymer may be a homopolymer or a copolymer, including random copolymer, block copolymer, or graft copolymer. The biodegradable polymer may be a linear polymer, a branched polymer, or a dendrimer. The biodegradable polymers may be of natural or synthetic origin.

Some non-limiting examples include suitable polysaccharides include cellulose, dextran, chitin, chitosan, alginate, pectin, mucilage, pullanan, methylcellulose, carboxymethylcullose, hydroxypropyl methylcellulose, hyaluronic acid (HA), hydroxyethyl methylcellulose, arabinoxylans, bacterial polysaccharides and combinations thereof. In certain embodiments, the detachable layer may comprise carboxymethylcellulose.

Some non-limiting examples of bioabsorbable materials used to form the substrate include to polymers selected from the group consisting of aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, for the purpose of this invention, aliphatic polyesters include, but are not limited to, homopolymers and copolymers of lactide (including lactic acid, D-,L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7, 14-dione); 1,5-dioxepan-2-one; 6,6-dimethyl- 1,4-dioxan-2-one; 2,5-diketomorpholine; pivalolactone; α,αdiethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Other suitable biodegradable polymers include but are not limited to poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

In certain embodiments, hydrogels comprising precursors, e.g., a monomer or a macromer, may be employed in the present disclosure. One type of precursor that may have a functional group that is an electrophile or nucleophile. The term "functional group" as used herein refers to groups capable of reacting with each other to form a bond. Electrophiles react with nucleophiles to form covalent bonds. In certain embodiments, a first set of electrophilic functional groups on a first precursor may react with a second set of nucleophilic functional groups on a second precursor.

Suitable electrophilic functional groups include, for example, N-hydroxysuccinimides, sulfosuccinimides, carbonyldiimidazole, sulfonyl chloride, aryl halides, sulfosuccinimidyl esters, N-hydroxysuccinimidyl esters, succinimidyl esters, epoxides, aldehydes, maleimides, imidoesters and the like. In embodiments, the electrophilic functional group is a succinimidyl ester.

Suitable nucleophilic groups which may be present include, for example, —$NH_2$, —SH, —OH, —$PH_2$, and —CO—NH—$NH_2$. Other examples of suitable precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated herein by reference.

Both the detachable layer and the polymeric layer may also consist of at least one optional ingredient. Some examples of suitable optional ingredients include emulsifiers, viscosity enhancers, dyes, pigments, fragrances, pH modifiers, wetting agents, plasticizers, antioxidants, and the like. The optional ingredients may represent up to about 10% of the detachable layer and/or polymeric layer by weight.

In some embodiments, the detachable layer may include at least one plasticizer, i.e., glycerol. For instance, the detachable layer may include a combination of carboxymethylcellulose and glycerol to form a detachable film.

The detachable films described herein may be formed by any suitable method known to those skilled in the art. In certain embodiments, a solution may be formed which includes the polysaccharide and any optional ingredients. The solution may be cast bulk sheet stock, spray coated using an ultrasonic sprayer, extruded, molded and the like, to form the detachable films described herein. Suitable solvents include, without limitation, methylene chloride, chloroform, N-methylpyrrolidone, tetrahydrofuran, dimethylformamide, methanol, ethanol, hexanes, acetone, water, buffers, saline, and combinations thereof.

In some embodiments, the detachable layer may be cast as a film directly on a portion of the medical device surface. In other embodiments, the detachable layer may be spray coated directly on a portion of the medical device surface. In still other embodiments, the detachable layer may be formed before being positioned onto the medical device. In yet another embodiment, the detachable film layer may be combined with the polymeric layer before being combined with the surface of the medical device.

The detachable film layers described herein may be designed to dissolve within a particular time range. For example, the detachable layer may be designed to dissolve within less than 72 hours of implantation. In some embodiments, the detachable layer may dissolve following implantation within a time frame ranging from about 5 seconds to about 24 hours. In certain embodiments, the detachable layer may dissolve following implantation from about 30 seconds to about 12 hours.

In some embodiments, the detachable film layer may not dissolve, but may hydrate and swell, separating from the substrate. For example, the detachable film may comprise a hydrogel. Suitable materials which may comprise hydrogels include those described herein.

The polymeric films described herein may be formed by any suitable method known to those skilled in the art. In certain embodiments, a solution may be formed which includes the polymer and any optional ingredients. The solution may be cast bulk sheet stock, spray coated using an ultrasonic sprayer, extruded, molded and the like, to form the polymeric film layers described herein. Suitable solvents include, without limitation, methylene chloride, chloroform, N-methylpyrrolidone, tetrahydrofuran, dimethylformamide, methanol, ethanol, hexanes, acetone and combinations thereof. The polymers may represent from about 0.1% to about 95% (w/w) of the polymeric film.

In certain embodiments, CMC may represent from about 0.1% to about 95% (w/w) of the detachable film. In some embodiments, the CMC may represent from about 1% to about 75% (w/w) of the detachable film.

In certain embodiments, collagen may represent from about 0.1% to about 95% (w/w) of the detachable film. In some embodiments, collagen may represent from about 1% to about 75% (w/w) of the detachable film.

In some embodiments, the polymeric film layer may be cast as a film directly on a portion of the detachable film and/or the medical device surface. In other embodiments, the polymeric film layer may be spray coated directly on a portion of the detachable film and/or the medical device surface. In still other embodiments, the polymeric layer may be formed before being positioned onto the medical device. In yet another embodiment, the polymeric film layer may be formed using an ultrasonic spraying nozzle onto an inert substrate.

In certain embodiments, the first or second layer may be created using a spraying technique, such as ultrasonic spraying. Spraying films results in a unique ability to include a high therapeutic payload of the therapeutic agent (>1 mg/cm$^2$). For example, the medical device as described herein may be fabricated by passing a first solution containing a hydrophobic polymer and a second solution containing a therapeutic agent through an ultrasonic spray nozzle to form droplets. The droplets may be mixed while falling towards or being depositioned onto an inert substrate, such as silicone sheet, or the detachable layer of medical device to form a film.

In some embodiments, the films include a single layer containing a hydrophobic polymer and a therapeutic agent. In other embodiments, the films include a first layer containing a hydrophobic polymer and a second layer containing a therapeutic agent. In still other embodiments, the films include a tri-layer structure wherein a second layer containing a therapeutic agent is positioned between a first layer containing a hydrophobic polymer and a third layer containing the same or different hydrophobic polymer.

In certain embodiments, the hydrophobic polymers of the films may include homopolymers or copolymers which include lactide, glycolide, dioxanone, trimethylene carbonate, and ε-caprolactone. For example, the therapeutic agents described herein may be combined with copolymers, i.e., random, or block copolymers, of lactide and glycolide or glycolide and ε-caprolactone. Increasing the amount of glycolide may increase the films degradation rate. While increasing the amount of lactide and/or caprolactone may extend the degradation/absorption profile of the film. For example, lactide rich copolymers, i.e., greater than about 50% lactide, may be particularly useful to enhance a particular polymer's solubility, such as glycolide.

The hydrophobic polymers used to form the films may initially form polymer solutions, including suspensions, emulsions, dispersions and the like, prior to being passed through an ultrasonic sprayer. Some non-limiting examples of solvents suitable for forming the polymer solutions may include methylene chloride, chloroform, N-methylpyrrolidone, tetrahydrofuran, dimethylformamide, methanol, ethanol, hexanes, acetone and combinations thereof. The polymer may represent from about 1.0% to about 25% (w/w) in the solution.

In some embodiments, the solvent used to form the hydrophobic polymer solution may not be the same solvent used to form the therapeutic agent solution. In some embodiments, the therapeutic agent is not miscible in the solvent used to form the polymer solution.

The term "therapeutic agent," as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic effect, such as, anti-adhesives, anti-microbials, analgesics, antipyretics, anesthetics (e.g. local and systemic), antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of agents may be used.

Other therapeutic agents, which may be included as a drug include: anti-fertility agents; parasympathomimetic agents; psychotherapeutic agents; tranquilizers; decongestants; sedative hypnotics; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; and immunological agents.

Other examples of suitable agents, which may be included in the films described herein include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (e.g., IL-2, IL-3, IL-4, IL-6); interferons (e.g., β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, and RNAi; oligonucleotides; polynucleotides; and ribozymes.

Some specific non-limiting examples of water-soluble drugs that may be used in the present polymeric films include, lidocaine, bupivicaine, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenyloin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cyclothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metoformin, buformin, orotic acid, azathioprine, lactulose, nitrogen mustard, cyclophophamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof.

The water-soluble drug may not need to be converted to a salt form, i.e., tetracycline hydrochloride. In some embodiments, the therapeutic agent may include an anesthetic, i.e., bupivicaine, lidocaine, benzocaine, and the like.

Although the above therapeutic agents have been provided for the purposes of illustration, it should be understood that the present disclosure is not so limited. In particular, although certain therapeutic agents are specifically referred to above, the present disclosure should be understood to include analogues, derivatives and conjugates of such agents.

The therapeutic agent may be combined with the medical device, the polymeric layer and/or the detachable layer. In some embodiments, the therapeutic agent may be included in the detachable layer to provide an immediate release of the therapeutic agent when the first layer dissolves. In some embodiments, the therapeutic agent may be included in the polymeric film to provide sustained release of the therapeutic agent following detachment from the substrate. Because the film may include a high payload of therapeutic agent, the polymeric films may provide sustained release of the agent for longer periods of time.

The water-soluble therapeutic agents may be combined with any suitable solvent to form a therapeutic solution. Some useful non-limiting examples include organic solvents such as methylene chloride, chloroform, N-methylpyrrolidone, tetrahydrofuran, dimethylformamide, methanol, ethanol, hexanes, acetone, water and combinations thereof. In some embodiments, the solvent for the therapeutic agent is not a co-solvent for the hydrophobic polymer. In some embodiments, the hydrophobic polymer is not miscible in the solvent for the therapeutic agent.

The water-soluble therapeutic agent may form a solution at a concentration ranging from about 1 microgram/ml to about 1 gram/ml. In certain embodiments, the concentration of the therapeutic solution may range from about 1 mg/ml to about 500 mg/ml. In still other embodiments, the concentration of the therapeutic solution may range from about 10 mg/ml to about 300 mg/ml. By solution, the therapeutic preparation is intended to include suspensions, emulsions, dispersions, and the like.

In forming the polymeric films, the therapeutic solution and the polymer solution may be passed through an ultrasonic spray nozzle. Ultrasonic sprayers include ultrasonic spray nozzles which may be used to generate vibrations leading to atomization of the solutions. The sprayer body consists of three principal sections: front horn, the atomizing section; rear horn, the rear section, and a section consisting of a pair of disc-shaped piezoelectric transducers. Working in unison, these three elements provide means for creating the vibration required to atomize the solutions delivered to the nozzle surface. The solutions enter through a fitting on the rear, passes through the tube and then the central axis of the front horn. Finally, the solution reaches the atomizing surface of the nozzle where atomization takes place. Piezoelectric transducers convert electrical energy provided by an external power source into high-frequency mechanical motion or vibration. The solution absorbs the underlying vibration energy and generates capillary waves. When the amplitude of the capillary waves exceeds a critical value, the waves collapse ejecting small droplets of the solutions.

The ultrasonic sprayer nozzle may include a variety of controls which may be adjusted to alter the characteristics of the polymeric films described herein. Some non-limiting examples include: vibration frequency, operational power; solution flow rates, nozzle speed, and length of movement of the nozzle. In forming the films described herein, the sprayer nozzle may vibrate at a frequency ranging from about 20 kHz to about 100 kHz and may operate at a power ranging from about 2 to 10 watts. In some embodiments, the sprayer nozzle may vibrate at a frequency of about 48 kHz and operate at a power of about 6 watts.

In certain embodiments, the ultrasonic spray nozzles may be movable. The nozzle may move a speed ranging from about 10 mm/sec to about 200 mm/sec. In other embodiments, the nozzle speed may range from about 50 mm/sec to about 150 mm/sec. In addition, the height of the movable nozzles may range from about 30 mm to about 60 mm from the inert substrate.

Also, the flow rate of the solutions passed through the sprayer nozzle may be varied within the range of about 0.1 ml/min to about 5 ml/min. In embodiments, the flow rate of the solutions may be within the range of about 0.5 ml/min and 2.0 ml/min. The flow rate may be different for each of the polymer solution and the therapeutic solutions. It is envisioned that each of the sprayer controls may be individually adjusted for each of the different solutions being passed therethrough.

Figure 3:
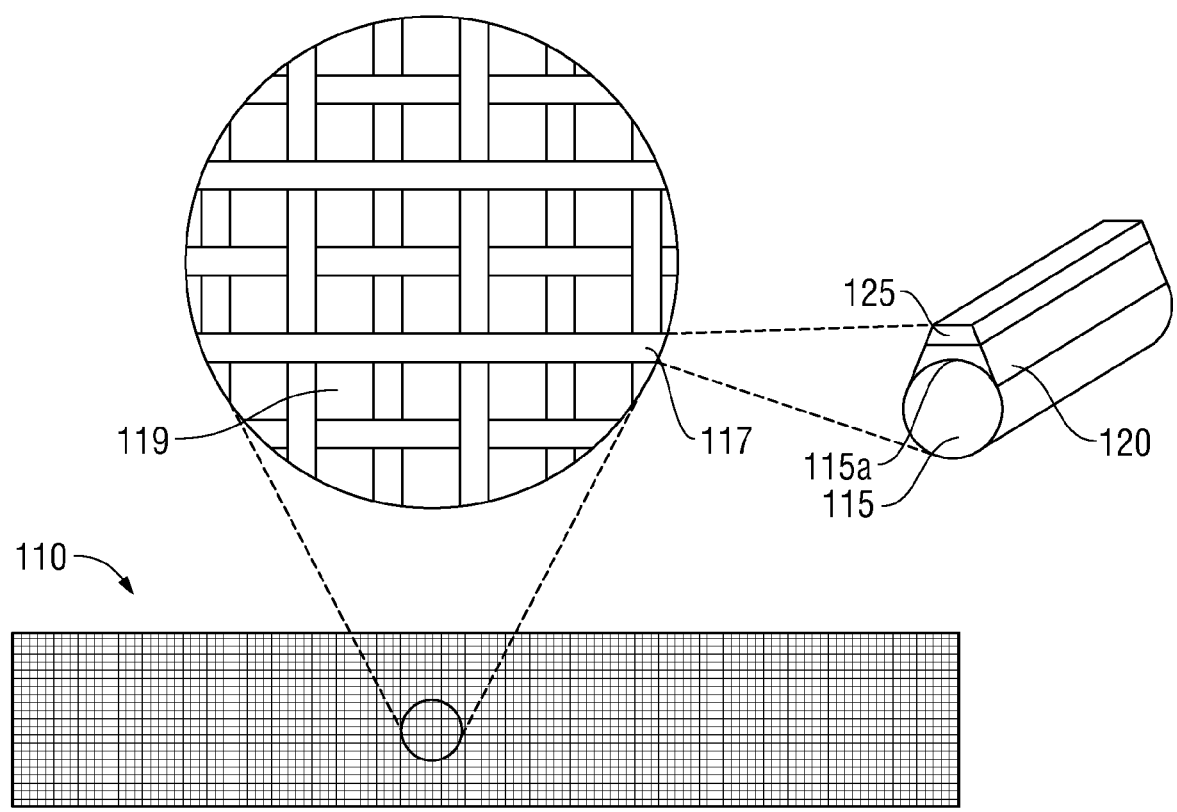
FIG. 3 is a top view of a medical device according to another embodiment described in the present disclosure.

Turning now to FIG. 3, medical device 110 includes substrate 115, i.e., a surgical mesh, having a surface 115a and including a network of interconnected filaments 117 which create pores 119. Detachable layer 120 is positioned on at least a portion of surface 115a of substrate 115. Second polymeric layer 125 is positioned on at least a portion of first detachable layer 120. Pores 119 are not occluded by detachable layer 120 and polymeric layer 125. As depicted in FIG. 3, no portion of polymeric layer 125 is connected to substrate 115, thus upon dissolution of detachable layer 120, polymeric layer 125 and substrate 115 will become detached or separated from one another to create an implantable medical device including substrate 115 and a polymeric film 125 displaying a porous configuration similar to substrate 115. At least one therapeutic agent may be positioned within the substrate, the detachable layer, and/or the polymeric layer.

Figure 4:
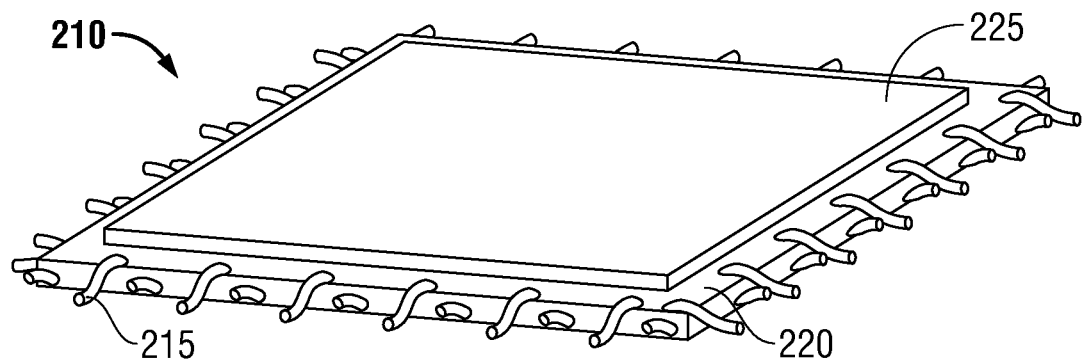
FIG. 4 is a perspective view of a medical device according to yet another embodiment described in the present disclosure.

In some embodiments, the porosity of the substrate may be occluded. For example, in FIG. 4, detachable layer 220 is positioned on surface 215 of medical device 210 in a manner which occludes at least a portion of the pores of medical device 210. It is envisioned that following implantation, detachable layer 220 will hydrate and dissolve into the bodily fluids detaching polymeric film layer 225 from substrate 215 to reveal the open pore structure and architecture of substrate 215, i.e., surgical mesh. In some embodiments, as further depicted in FIG. 4, polymeric layer 225 may be a different size or dimension than detachable layer 220.

Figure 5:
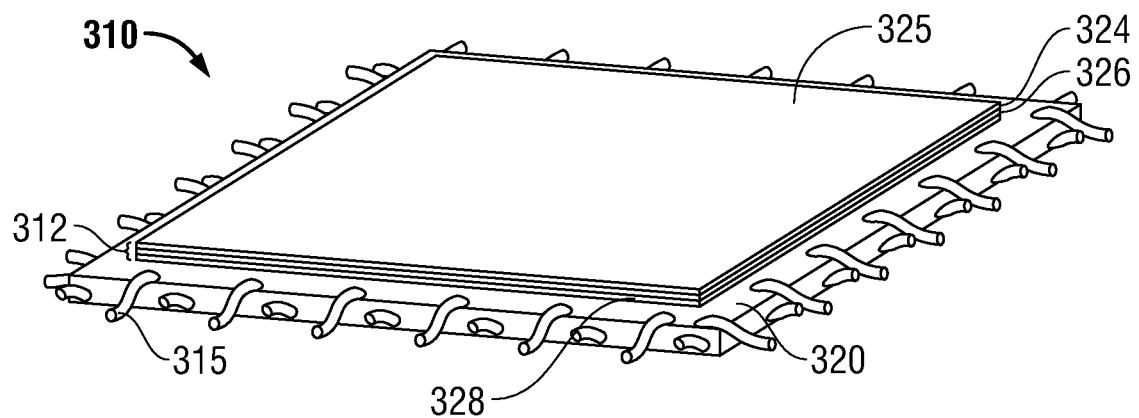
FIG. 5 is a perspective view of a medical device according to still another embodiment described in the present disclosure.

Looking to FIG. 5, medical device 310 includes substrate 315, detachable layer 320 and polymeric film layer 325. Polymeric film layer 325 is shown as a film which includes tri-layer structure 312 which contains first layer 324, second layer 326, and third layer 328. First layer 324 may include at least one hydrophobic polymer and second layer 326 may include at least one water-soluble therapeutic agent. Third layer 328 may include the same or different hydrophobic polymer as included in first layer 324. For example, in some embodiments, second layer 326 may include a therapeutic agent, such as bupivacaine, and the first and third layers may include the same hydrophobic polymer material, i.e., poly(glycolide-co-caprolactone). In another example, all three layers may include the same polymer material, i.e., poly(glycolide-co-caprolactone) and second layer 326 may also include a highly water-soluble therapeutic agent, i.e.

Figure 6:
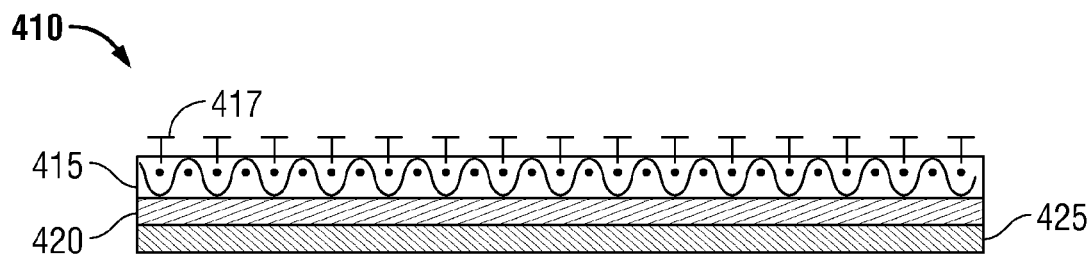
FIG. 6 is a side view of a medical device according to another embodiment described in the present disclosure.
Figure 7:
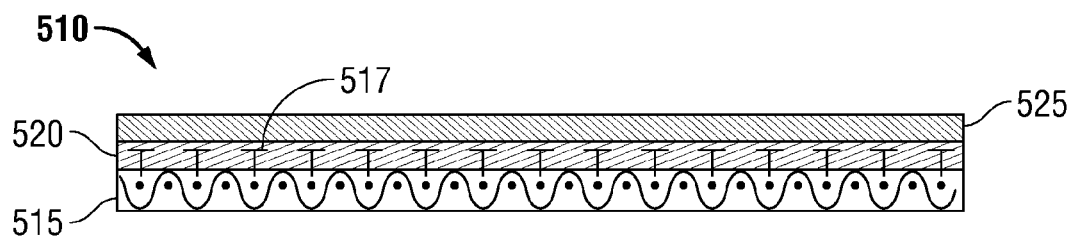
FIG. 7 is a side view of a medical device according to yet another embodiment described in the present disclosure.

In FIG. 6, medical device 410 is a surgical mesh 415 which includes a plurality of spiked naps 417 for grabbing tissue and/or other portions of the mesh. Detachable film layer 420 and polymeric film layer 425 are positioned on a portion of surgical mesh 415 which does not include spiked naps 417. However, in embodiments, such as those shown in FIG. 7, detachable layer 520 and polymeric layer 525 may be positioned on a portion of surgical mesh 515 which includes spiked naps 517. This embodiment may be advantageous when mesh fixation can be delayed. For example, the surgeon has time to position the mesh and once positioned, the detachable layer can dissolve, enabling the spiked naps 517 to anchor mesh in the predetermined position.

Figure 8:
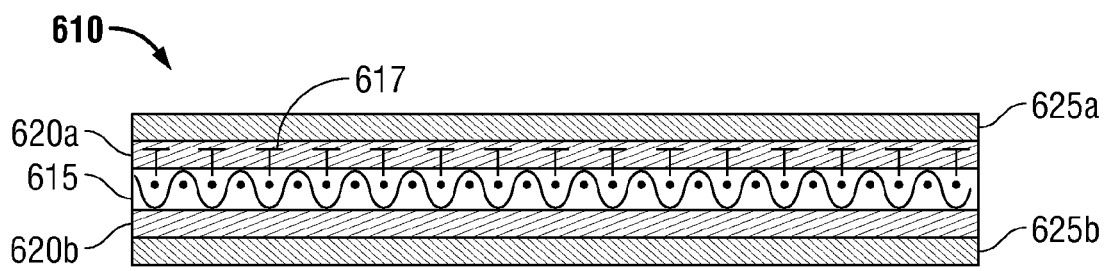
FIG. 8 is a side view of a medical device according to still another embodiment described in the present disclosure.

In still other embodiments, as those shown in FIG. 8, medical device 610 may include more than one detachable layer 620*a* and 620*b* and/or more than one polymeric layer 625*a* and 625*b*. Of course, as noted herein, at least one therapeutic agent may be included into any of the medical device, detachable layer, polymeric layer and combinations thereof for delivery of the therapeutic agent upon implantation.

Figure 9:
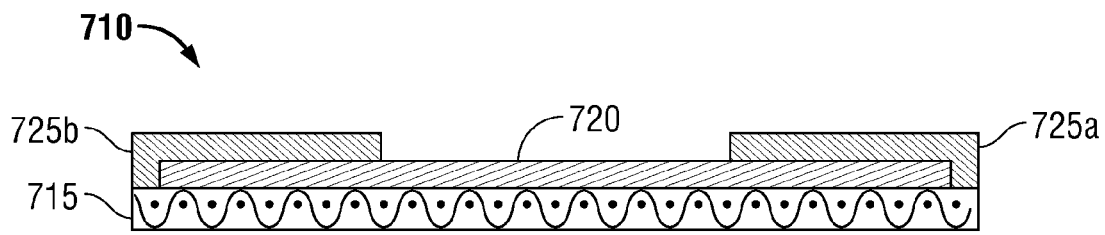
FIG. 9 is a side view of a medical device according to another embodiment described in the present disclosure.

FIG. 9 depicts another embodiment, wherein polymeric layers 725*a* and 725*b* may be attached to a portion of detachable layer 720 and also a portion of substrate 715 of medical device 710. In such embodiments, dissolution of detachable layer 720 detaches only a portion of polymeric layer 725 from substrate 715 thereby leaving open pores between polymeric layer 725 and substrate 715 which may allow for the ingrowth of tissue.

Figure 10A:
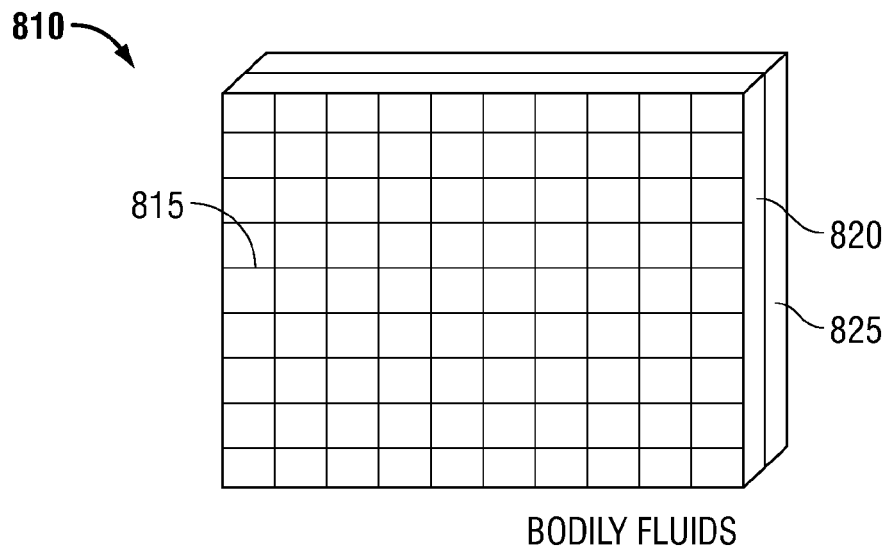
FIGS. 10A and 10B are perspective views of a medical device according to still another embodiment described in the present disclosure.
Figure 10B:
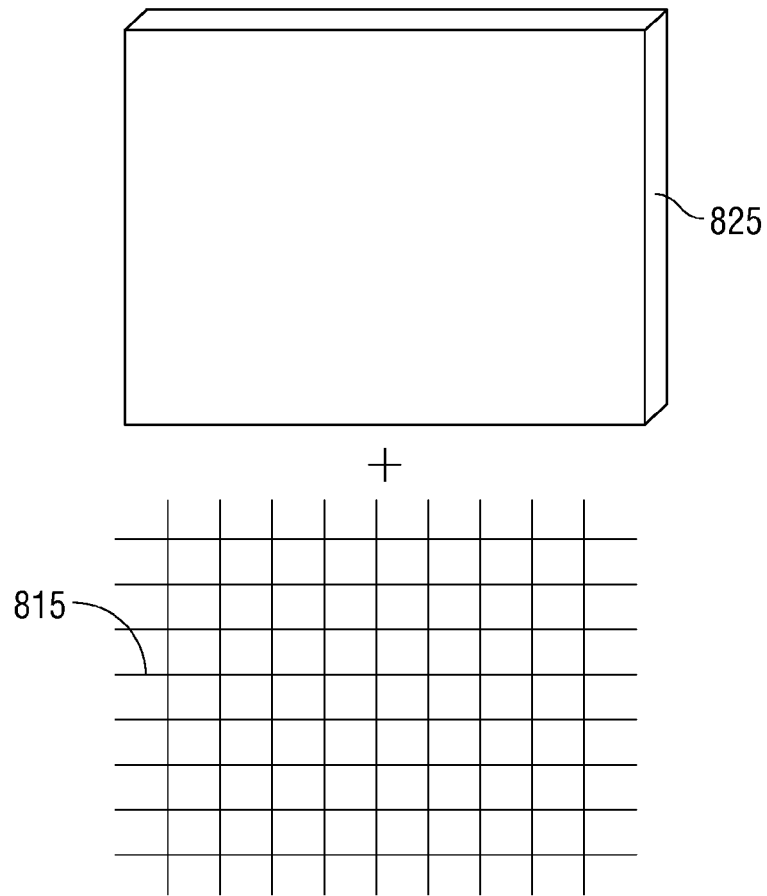

As shown in FIGS. 10A and 10B, medical device 810, which includes substrate 815, detachable layer 820 and polymeric film layer 825, will separate into multiple parts following implantation and/or exposure to bodily fluids, including water, blood, mucous, saline, dextrose and the like. Detachable layer 820 will hydrate and dissolve into the bodily fluids detaching polymeric film layer 825 from substrate 815 to create multiple, separate implantable medical devices, i.e., a mesh 815 and a film 825 for delivery of a therapeutic agent (not shown), as illustrated in FIG. 10B.

Figure 11:
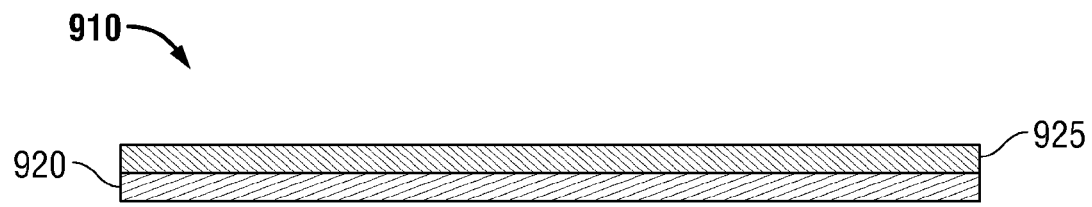
FIG. 11 is a side view of a medical device according to another embodiment described in the present disclosure.

FIG. 11 depicts medical device 910 which includes detachable layer 920 and polymeric film layer 925. Polymeric layer 925 is positioned on at least a portion of detachable layer 920. In some embodiments, detachable layer 920 may dissolve in situ to leave only polymeric film layer 925 at the site of implantation.

Figure 12A:
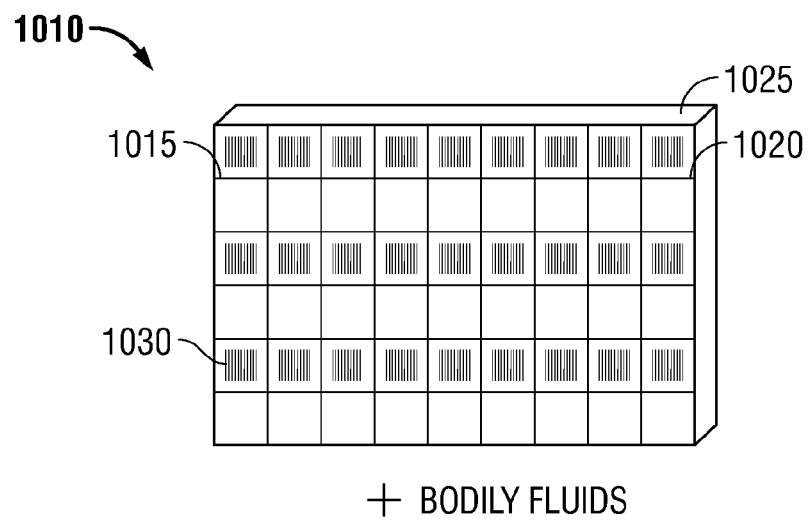
FIGS. 12A-12C are perspective views of a medical device according to still another embodiment described in the present disclosure.
Figure 12B:
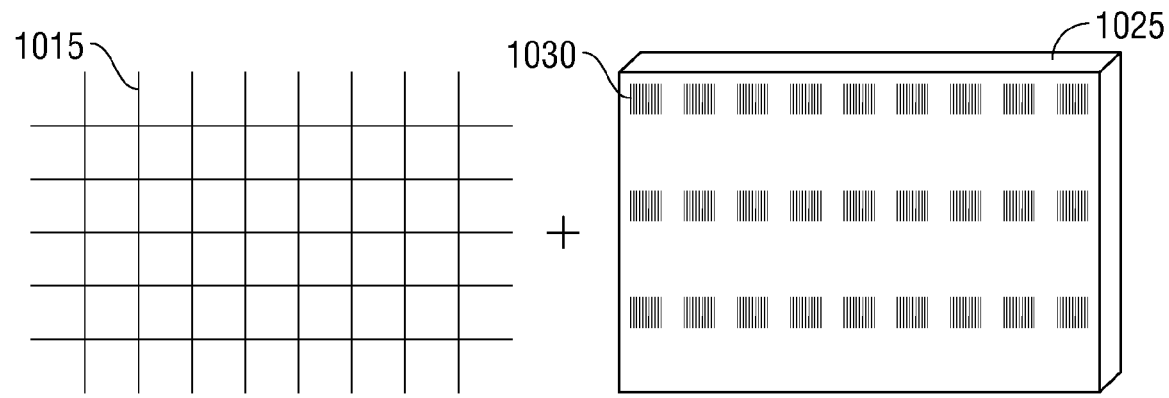
Figure 12C:
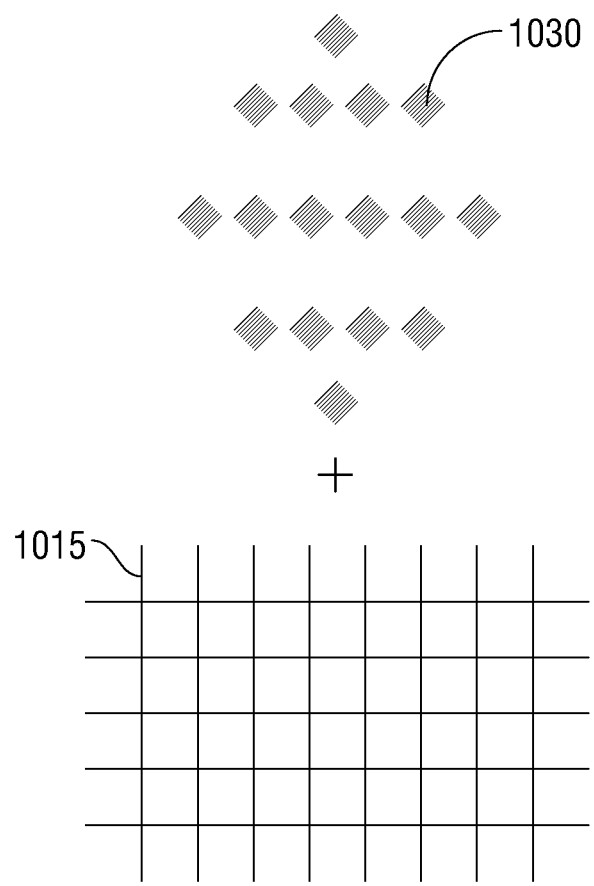

As depicted in FIGS. 12A, 12B and 12C, medical device 1010, which includes substrate 1015, detachable layer 1020, polymeric film layer 1025 and therapeutic agents 1030, will separate into multiple parts following implantation and/or exposure to bodily fluids, including water, blood, mucous, saline, dextrose and the like. Detachable layer 1020 will hydrate and dissolve into the bodily fluids detaching polymeric film layer 1025 along with therapeutic agent 1030 from substrate 1015 to create multiple, separate implantable medical devices, i.e., a mesh 1015 and a film 1025 for delivery of a therapeutic agents 1030, as shown in FIG. 12B. Over time, film 1025 will degrade and/or dissolve releasing therapeutic agent 1030 from film 1025 (see FIG. 12C).

The medical devices described herein may be formed by combining any combination of individual parts. For example, a detachable film including glycerol and carboxymethylcellulose and/or collagen may be prepared via solution casting, and a polymeric layer including poly(glycolide-ε-caprolactone) may formed via solution spraying through an ultrasonic spray nozzle, and a three-dimensional mesh as shown in FIG. 1 may be knit individually. The detachable and polymeric films may be dried and cut or punched to size and connected to a surface of the mesh via any combination of heat, compression, adhesives, mechanical interlocking, and the like.

In another example, the detachable film layer and the polymeric layer may be formed together. The surface of the medical device may be put into contact with the detachable layer prior to drying to attach the substrate to the detachable layer which is attached to the polymeric layer.

In yet another example, the substrate and the multiple layers may be formed at the same time as a monolithic structure.

The medical devices described herein may be used to deliver therapeutic agents in the body. The delivery of the agents may be immediate or sustained over time. In embodiments, the self-detachable medical devices described herein may be implanted and include a detachable layer, a polymeric layer and at least one therapeutic agent included in one of the two layers.

It will be understood that various modifications may be made to the embodiments disclosed herein. For example, in embodiments the medical device may rolled prior to being delivered into the body via a cannula, trocar or laparoscopic delivery device. In another example, the medical devices described herein may be sterilized and packaged into using any suitable sterilization process, i.e., gamma radiation, and any suitable medical device package, i.e., an injectable medical device package. Thus, those skilled in the art will envision other modifications within the scope and spirit of the claims.

What is claimed is:
1. A medical device comprising:
an implantable substrate having a surface, a first detachable layer positioned on at least a portion of the surface, and a second polymeric layer positioned on at least a portion of the first detachable layer, wherein the first detachable layer is configured to dissolve within less than 72 hours following implantation to separate the implantable sub- strate from the second polymeric layer to form multiple implantable medical devices.

2. The medical device of claim 1, wherein at least one of the first detachable layer and the second polymeric layer comprises at least one therapeutic agent.

3. The medical device of claim 2, wherein the at least one therapeutic agent is selected from the group consisting of anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, enzymes, and combinations thereof.

4. The medical device of claim 2, wherein the at least one therapeutic agent comprises bupivicaine, cisplatin, fluorouracil, methotrexate, capsaicin and combinations thereof.

5. The medical device of claim 2, wherein the at least one therapeutic agent comprises bupivicaine hydrochloride.

6. The medical device of claim 1, wherein the implantable substrate is selected from the group consisting of sutures, staples, pledgets, buttresses, meshes, clamps, pins, screws, anchors, and occlusion devices.

7. The medical device of claim 1, wherein the implantable substrate comprises a surgical mesh.

8. The medical device of claim 1, wherein the first detachable layer is selected from the group consisting of polysaccharides, proteins, peptides and combinations thereof.

9. The medical device of claim 8, wherein the polysaccharide is selected from the group consisting of cellulose, dextran, chitin, chitosan, alginate, pectin, mucilage, pullalan, methylcellulose, carboxymethylcullose, hydroxypropyl methylcellulose, hydroxyethyl methylcellulose, arabinoxylans, bacterial polysaccharides and combinations thereof.

10. The medical device of claim 8, wherein the protein is selected from the group consisting of collagen, elastin, fibrin, fibrinogen, silk, albumin, and combinations thereof.

11. The medical device of claim 8, wherein the protein comprises collagen.

12. The medical device of claim 1, wherein the first detachable layer comprises a hydrogel.

13. The medical device of claim 1, wherein the first detachable layer comprises a water soluble polymer.

14. The medical device of claim 1, wherein the first detachable layer further comprises at least one optional ingredient.

15. A medical device comprising:
a surgical mesh having a surface,
a first detachable layer positioned on at least a portion of the surface, and
a second polymeric layer positioned on at least a portion of the first detachable layer, wherein within less than 72 hours after implantation, the first detachable layer dissolves separating the surgical mesh from the second polymeric layer to form multiple implantable medical devices.

16. The medical device of claim 15, wherein at least one of the first detachable layer and the second polymeric layer includes at least one therapeutic agent.

17. The medical device of claim 16, wherein the at least one therapeutic agent comprises bupivicaine, cisplatin, fluorouracil, methotrexate, capsaicin and combinations thereof.

18. The medical device of claim 16, wherein the at least one therapeutic agent comprises bupivicaine hydrochloride.

19. The medical device of claim 15, wherein the second polymeric layer comprises an absorbable polymer.

20. The medical device of claim 15, wherein the first detachable layer comprises collagen.

21. The medical device of claim 15, wherein the surgical mesh further comprises a plurality of spiked naps.

22. The medical device of claim 21, wherein the first detachable layer and the second polymeric layer are positioned on a portion of the surgical mesh which does not include the plurality of spiked naps.

23. The medical device of claim 21, wherein the first detachable layer and the second polymeric layer are positioned on a portion of the surgical mesh which includes the plurality of spiked naps.

24. A method of delivery a therapeutic agent comprising:
implanting a self-detachable medical device having a first detachable layer positioned on at least a portion of the medical device,
a second polymeric layer positioned on at least a portion of the first detachable layer, and
at least one therapeutic agent included in at least one of the first detachable layer and the second polymeric layer, wherein the first detachable layer is configured to dissolve within less than 72 hours following implantation to separate the medical device from the second polymeric layer to form multiple implantable medical devices.

* * * * *